US 6,550,305 B2

(12) United States Patent
Tomisawa

(10) Patent No.: US 6,550,305 B2
(45) Date of Patent: Apr. 22, 2003

(54) ACTIVATION DIAGNOSIS METHOD AND ACTIVATION DIAGNOSIS APPARATUS FOR AIR-FUEL RATIO SENSOR

(75) Inventor: Naoki Tomisawa, Atsugi (JP)

(73) Assignee: Unisia Jecs Corporation, Kanagawa-Ken (JP)

( * ) Notice: Subject to any disclaimer, the term of this patent is extended or adjusted under 35 U.S.C. 154(b) by 0 days.

(21) Appl. No.: 10/241,480

(22) Filed: Sep. 12, 2002

(65) Prior Publication Data

US 2003/0010088 A1 Jan. 16, 2003

Related U.S. Application Data

(62) Division of application No. 09/452,127, filed on Dec. 1, 1999, now Pat. No. 6,453,720.

(30) Foreign Application Priority Data

Dec. 16, 1998 (JP) .......................................... 10-358231

(51) Int. Cl.[7] .......................................... G01N 27/419
(52) U.S. Cl. ....................... 73/1.06; 204/401; 205/784.5
(58) Field of Search ................... 73/1.06, 1.02, 73/23–32, 118.2, 119 A; 701/101, 103, 105, 109; 374/1, 36, 37, 45, 54; 204/421, 427, 428, 429; 205/784.5

(56) References Cited

U.S. PATENT DOCUMENTS

| 5,172,677 | A | 12/1992 | Suzuki ....................... 123/688 |
| 5,172,678 | A | 12/1992 | Suzuki ....................... 123/688 |
| 5,340,462 | A | 8/1994 | Suzuki ....................... 204/425 |
| 5,385,517 | A | 1/1995 | Horo et al. ................ 477/169 |
| 5,517,848 | A | 5/1996 | Hosuya et al. ............. 73/23.31 |
| 5,700,367 | A | 12/1997 | Yamada et al. ............. 205/785 |
| 5,719,778 | A | 2/1998 | Suzumura et al. ............ 700/207 |
| 5,850,811 | A | 12/1998 | Tomisawa et al. ......... 123/90.15 |
| 5,895,591 | A | 4/1999 | Kojima et al. ............. 73/31.05 |
| 5,922,226 | A | 7/1999 | Mizusawa et al. ........... 219/207 |
| 5,935,399 | A | * | 8/1999 | Tanaka et al. ........... 204/427 X |
| 5,976,350 | A | 11/1999 | Yamaan et al. ........... 205/784.5 |
| 5,979,157 | A | * | 11/1999 | Kinugasa et al. ............. 60/274 |
| 6,083,369 | A | * | 7/2000 | Tanigawa .................... 204/424 |
| 6,205,989 | B1 | 3/2001 | Aoki ....................... 73/1.07 X |
| 6,210,641 | B1 | 4/2001 | Yamada et al. ................ 422/94 |

FOREIGN PATENT DOCUMENTS

| JP | 60-162041 | 8/1985 | .................. 123/674 |
| JP | 60-240840 | 11/1985 | .................. 123/686 |
| JP | 63-167061 | 7/1988 | .................... 24/38 |
| JP | 1-124758 | 5/1989 | ................. 73/23.32 |
| JP | 1-177434 | 7/1989 | .................. 123/688 |
| JP | 3-246461 | 11/1991 | .................. 324/378 |
| JP | 6-323185 | 11/1994 | |
| JP | 8-226412 | 9/1996 | |

* cited by examiner

*Primary Examiner*—Thomas P. Noland
(74) *Attorney, Agent, or Firm*—McDermott, Will & Emery

(57) ABSTRACT

Before starting an air-fuel ratio feedback control utilizing an air-fuel ratio sensor, activation of a wide-range air-fuel ratio sensor in an internal combustion engine is diagnosed by calculating heat transferred to and from the air-fuel ratio sensor, the output value of the wide-range air-fuel ratio sensor varies in response to oxygen concentration in exhaust which varies according to the air-fuel ratio of an intake air-fuel mixture of the internal combustion engine. The activation time from the starting of the engine until the air-fuel ratio sensor is activated is estimate based on the calculated result of the heat transfer. Alternatively, activation of the sensor is diagnosed under the condition that an output voltage of the oxygen concentration detecting unit of the sensor is fixed to a value either equal to or above a rich-side set voltage or equal to or under a lean-side set voltage, before starting the air-fuel ratio feedback control.

9 Claims, 6 Drawing Sheets

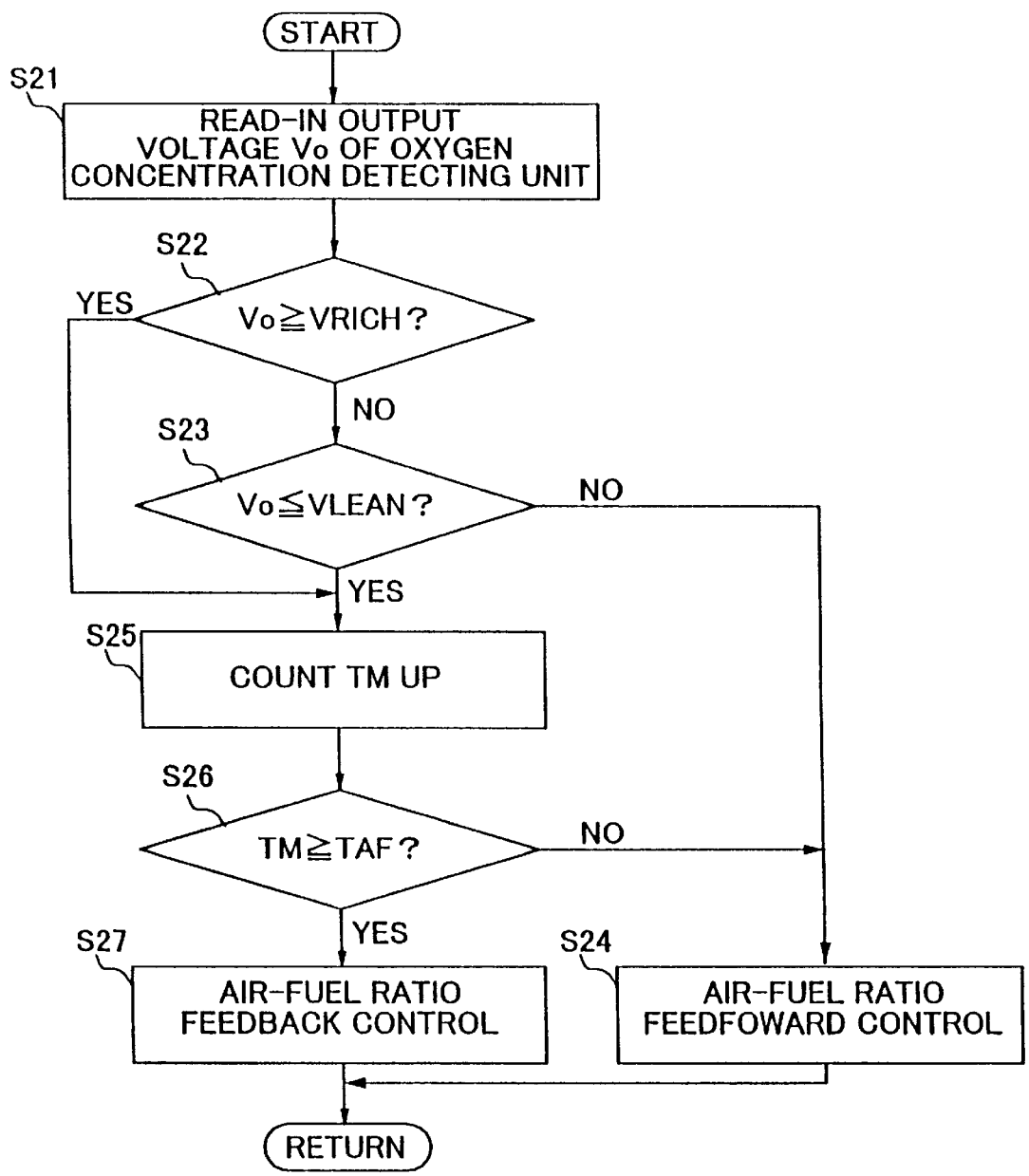

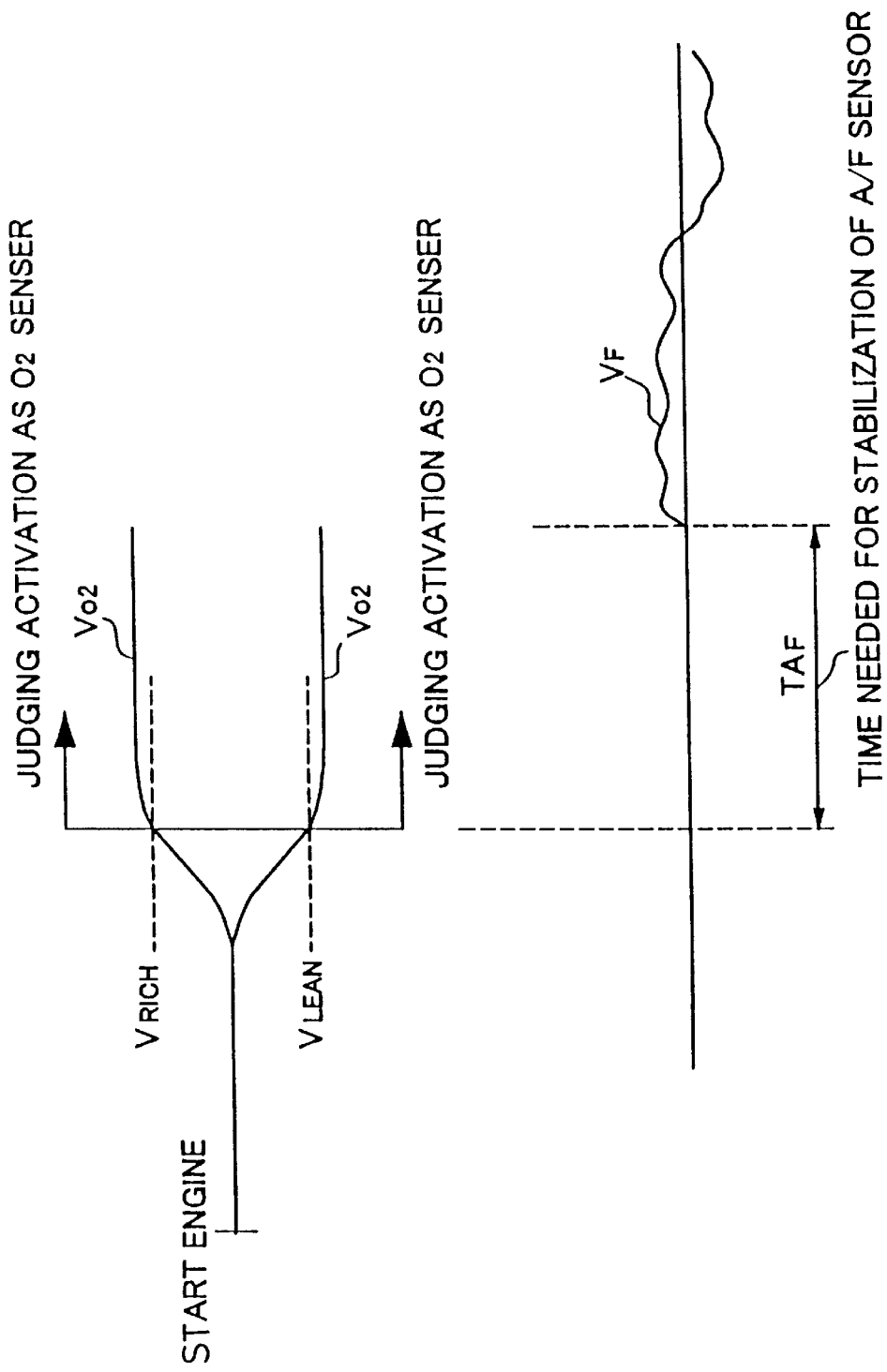

ACTIVATION DIAGNOSIS METHOD AND ACTIVATION DIAGNOSIS APPARATUS FOR AIR-FUEL RATIO SENSOR

This application is a divisional of application Ser. No. 09/452,127 filed Dec. 1, 1999 U.S. Pat. No. 6,453,720.

FIELD OF THE INVENTION

The present invention relates to a technique for diagnosing whether a wide-range type air-fuel ratio sensor to be used for an air-fuel ratio feedback control in an internal combustion engine is activated or not.

DESCRIPTION OF THE RELATED ART

Heretofore, an air-fuel ratio feedback control method is known where the air-fuel ratio of an engine intake air-fuel mixture is detected indirectly by detecting the oxygen concentration in an engine exhaust through an oxygen sensor, and controlling the fuel supply quantity so that the air-fuel ratio detected through the oxygen sensor approximates a target air-fuel ratio (refer for example to Japanese Unexamined Patent Publication No. 60-240840).

In the above-mentioned conventional air-fuel ratio feedback control, a method is generally performed where an oxygen sensor for detecting the rich/lean of the air-fuel ratio in comparison to the theoretical air-fuel ratio is utilized so as to control a target air-fuel ratio to the theoretical air-fuel ratio. However, in correspondence to the recent increase in demand for the improvement of exhaust emission performance or the improvement of fuel economy, a lean burn engine is being developed having a target air-fuel ratio which is set to a value much higher than the theoretical air-fuel ratio (for example, 20–24). In such an engine, a wide-rang type air-fuel ratio sensor capable of detecting a wide range of air-fuel ratio regions is utilized as the oxygen sensor.

Heretofore, generally in such air-fuel ratio feedback control, judgement is made as to whether the oxygen sensor is at an activated state, so that good output characteristics of the oxygen sensor may be gained before starting the air-fuel ratio feedback control based on the output value, thereby performing the control with high accuracy.

In the case of an oxygen sensor for detecting the rich/lean state of the air-fuel ratio to the theoretical air-fuel ratio by an on/off method, the activation status of the oxygen sensor may be judged by the output value (output voltage) being fixed either to the upper limit value on the rich side or to the lower limit value on the lean side.

However, in the case of a wide-range type air-fuel ratio sensor capable of detecting a wide range of air-fuel ratio regions, after the sensor is activated, the detection signal corresponding to the air-fuel ratio neighborhood (for example, the theoretical air-fuel ratio neighborhood) at the time is output, but since the variation range of the output value is small, the determination of the activation status of the sensor is difficult. Therefore, conventionally, it was common to wait for the lapse of a predetermined time after the start of engine operation, in which time the air-fuel sensor is considered to have been sufficiently activated, before shifting to the air-fuel ratio feedback control. However, in the above method, the predetermined time is set to a large value for leaving a considerable latitude, so that the air-fuel ratio sensor is judged to have been sufficiently activated even according to the operating condition where the activation is most delayed. Accordingly, in practice, there is a long period of time until the air-fuel ratio feedback control is started after the activation of the sensor. This is against the aim of using a wide-range air-fuel ratio sensor, which is to improve the exhaust emission performance.

The present invention aims at solving the above problems. The object of the invention is to diagnose the activation status of the wide-range air-fuel ratio sensor with high accuracy.

Further object of the present invention is to start the air-fuel ratio feedback control at an earlier stage, and to improve the exhaust emission performance, by improving the accuracy of the diagnosis.

SUMMARY OF THE INVENTION

In order to achieve the above object, a first activation diagnosis method according to the present invention comprises the steps of:

calculating heat transferred to and from a wide-range type air-fuel ratio sensor, an output value of the sensor being varied in response to oxygen concentration in exhaust which varies according to an air-fuel ratio in an intake air-fuel mixture of an internal combustion engine;

estimating the activation time from the starting of operation of the engine until the air-fuel ratio sensor is activated, based on the calculated heat transferred to and from the air-fuel ratio sensor; and diagnosing that the air-fuel ratio sensor is activated when the estimated activation time has passed after the starting of operation of the engine.

Further, a first activation diagnosis apparatus according to the present invention comprises each device or means for performing each function in the first activation diagnosis method.

According to the first diagnosis method or the first diagnosis apparatus, since it is possible that the heat transferred to and from the air-fuel ratio sensor is calculated, and based on the result of calculation, the heat increase characteristic of the air-fuel ratio sensor is estimated, the time necessary for the air-fuel ratio sensor to be activated may also be estimated. After the estimated activation time has passed from the starting of operation of the engine, the air-fuel ratio sensor is diagnosed as being activated, and an air-fuel ratio feedback control based on the air-fuel ratio sensor can be started.

With this construction, the activation status of the air-fuel ratio sensor may be diagnosed with high accuracy, and the air-fuel ratio feedback control may be started at a considerably early stage, thereby improving the exhaust emission performance.

Further, the estimation of the activation time may be performed based on at least two data selected from an environmental temperature at the starting time of the engine, a heat generation quantity of a heater installed to the air-fuel ratio sensor, and a heat quantity of the exhaust.

Since the environmental temperature at the starting time of the engine relates to a heat radiation quantity from the air-fuel ratio sensor, and the heat generation quantity of the heater and the heat quantity of the exhaust relate to a heat quantity to be supplied to the air-fuel ratio sensor, the time required for the air-fuel ratio sensor to be activated may be accurately estimated based on at least two parameters out of the above three parameters.

Moreover, the environmental temperature at the starting time of the engine may be either an ambient temperature or a cooling water temperature for cooling the engine.

Further, the estimation of the activation time may be calculated by the following equation:

activation time $T = T_o - TA - TB$;

wherein To represents a reference activation time calculated based on the environmental temperature at the starting time of the engine, TA represents an activation shortening time corresponding to the heat generation quantity of the heater, and TB represents an activation shortening time corresponding to the heat quantity of the exhaust.

With this construction, the heat transferred to and from the air-fuel ratio sensor may be calculated as accurately as possible by referring to all of the environmental temperature at the starting time of the engine, the heat generation quantity of the heater and the heat quantity of the exhaust. Thereby, the activation of the air-fuel ratio sensor may be diagnosed with a high degree of accuracy.

In the present invention, the lower the environmental temperature at the starting time of the engine is, the greater the calculated value of the reference activation time To is calculated. The reason for this is because the time needed for activation of the sensor is increased when the environmental temperature is decreased, which leads to increase of the heat quantity to be radiated from the air-fuel ratio sensor.

Further, the activation shortening time TA corresponding to the heat generation quantity of the heater is calculated as a value proportional to the power consumption of the heater. Since the heat generation quantity of the heater is proportional to the consumption of power, the heat generation quantity of the heater may be calculated with high accuracy by multiplying a constant by the consumed power calculated by multiplying the voltage by the current (or the power supply duty in the case of a duty control).

Moreover, the activation shortening time TB corresponding to the heat quantity of the exhaust is calculated by multiplying a basic value set proportionally to an intake air quantity of the engine by a correction coefficient calculated based on the engine rotation speed. That is, the heat quantity of the exhaust being supplied to the air-fuel ratio sensor is basically proportional to a flow quantity of the exhaust when assuming that the air-fuel ratio is constant. Therefore, a basic value equivalent to the flow quantity of the exhaust and proportional to the intake air quantity detected for the control of the engine is calculated, and the basic value is corrected in correspondence to the speed of flow of the exhaust based on the engine rotation speed, so as to gain an accurate calculation result.

With a second activation diagnosis method, there is provided an activation diagnosis method for a wide-range type air-fuel ratio sensor, the air-fuel ratio sensor being equipped with an oxygen concentration detecting unit formed of a solid electrolyte and outputting detection signals corresponding to oxygen concentration inside a hollow chamber to which exhaust of an internal combustion engine is introduced, and an oxygen pump unit for pumping oxygen into or out of the hollow chamber by controlling a current being applied to a solid electrolyte wall separating the hollow chamber and the exhaust side of the engine so as to control the oxygen concentration inside the hollow chamber to predetermined oxygen concentration, the air-fuel ratio sensor detecting the current being applied to the solid electrolyte wall to output an air-fuel ratio signal corresponding to the oxygen concentration in the exhaust; the activation diagnosis method comprising the steps of:

monitoring an output voltage of the oxygen concentration detecting unit after the starting of operation of the engine;

judging whether or not the output voltage of the oxygen concentration detecting unit is fixed to either a value equal to or above a rich-side set voltage or a value equal to or below a lean-side set voltage; and diagnosing that the air-fuel ratio sensor is activated under the condition that a status is detected where the output voltage of the oxygen concentration detecting unit is fixed to either a value equal to or above a rich-side set voltage or a value equal to or below a lean-side set voltage.

Further, a second activation diagnosis apparatus according to the present invention comprises each device or means for performing each function in the second activation diagnosis method.

According to the second diagnosis method or the second diagnosis apparatus, the oxygen concentration detecting unit functions as an oxygen sensor for judging the rich/lean state of the air-fuel ratio to the theoretical air-fuel ratio by an on/off method.

Therefore, as explained above, while the output voltage of the oxygen concentration detecting unit functioning as the oxygen sensor is monitored, when the output voltage is detected to be in a state fixed either to a value equal to or above a rich-side set voltage or a value equal to or below a lean-side set voltage, the air-fuel ratio sensor may be diagnosed to be substantially activated. Therefore, the air-fuel ratio sensor may be diagnosed as activated after the above judgement, and the air-fuel ratio feedback control based on an air-fuel ratio sensor may be started.

Accordingly, the activation of the air-fuel ratio sensor may be diagnosed with a high degree of accuracy, and the air-fuel ratio feedback control may be started at a very early stage, so the exhaust emission performance of the engine may be improved.

Further, the activation of the air-fuel ratio sensor may be diagnosed when a predetermined time has passed after detecting the status where the output voltage of the oxygen concentration detecting unit is fixed to either a value equal to or above a rich-side set voltage or a value equal to or below a lean-side set voltage.

Actually, the output of the wide-range air-fuel ratio sensor is stabilized when some time has passed for the temperature of the air-fuel ratio sensor as a whole (including the Nernst unit and the like) to stabilize after the oxygen concentration detecting unit functioning as the oxygen sensor is activated. Therefore, the air-fuel ratio sensor is diagnosed to be activated after the above-explained predetermined time has passed, to start the air-fuel ratio feedback control based on the air-fuel ratio sensor, thereby enabling the air-fuel ratio feedback control to be started at an even more stabilized status.

Here, the predetermined time may be set based on the heat transferred to and from the air-fuel ratio sensor. Thereby, the predetermined time needed for the temperature of the air-fuel ratio sensor as a whole to stabilize may be set more accurately, and the activation diagnosis accuracy for the air-fuel ratio sensor may be improved even further.

BRIEF DESCRIPTION OF THE DRAWINGS

FIG. 5 is a flowchart showing the activation diagnosis routine for the air-fuel ratio sensor according to a second embodiment; and FIG. 6 is a time chart showing the variation of output voltage Vo$_2$ of the oxygen concentration detecting unit and the output voltage $V_F$ of the air-fuel ratio sensor in the second embodiment.

DETAILED DESCRIPTION OF THE PREFERRED EMBODIMENT

A preferred embodiment of the present invention will now be explained with reference to the accompanied drawings.

Figure 1:
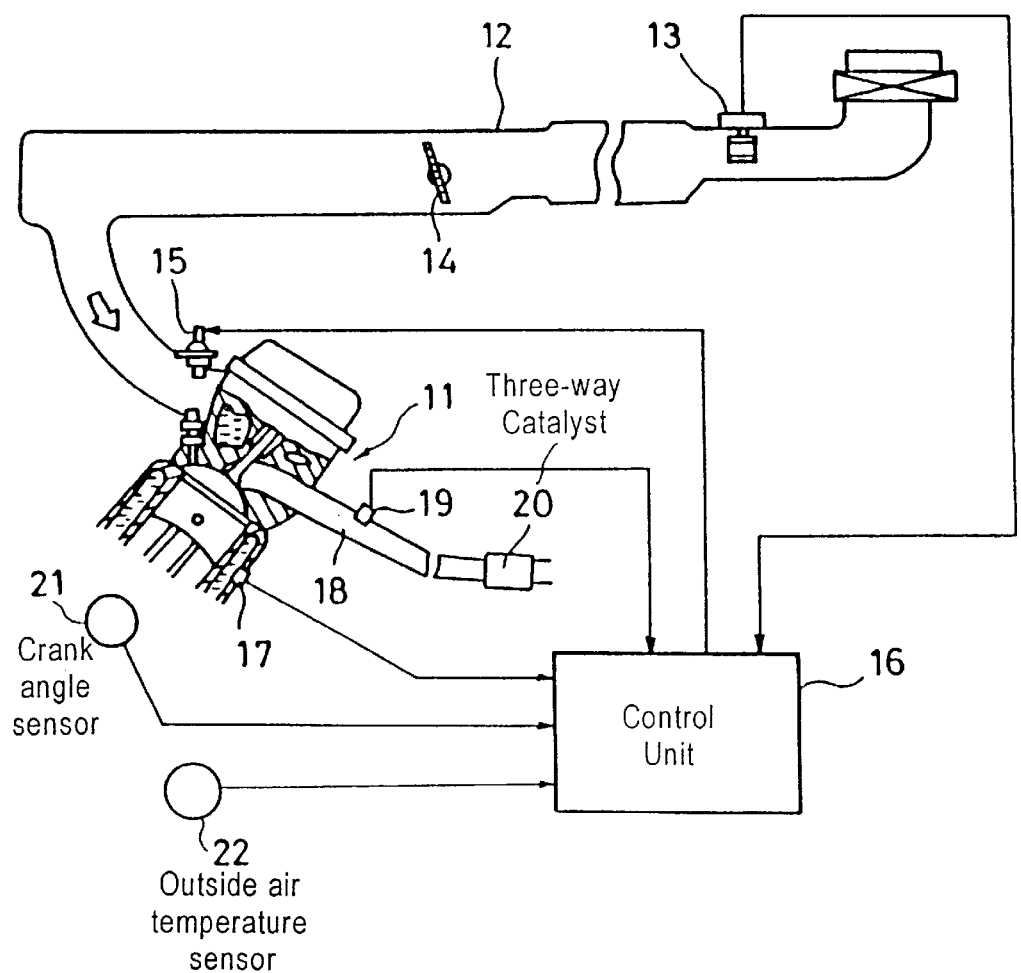
FIG. 1 is a diagram showing the system structure of an embodiment according to the present invention.

FIG. 1 shows the system structure according to one embodiment of the invention, wherein an intake passage 12 of an engine 11 is equipped with an airflow meter 13 for detecting an intake airflow quantity Qa and a throttle valve 14 for controlling the intake airflow quantity Qa in linkage with an accelerator pedal, and an electromagnetic fuel injection valve 15 is equipped as a fuel supply device to each cylinder at a manifold portion in the lower stream of the engine.

The fuel injection valve 15 is driven to open by an injection pulse signal generated from a control unit 16 containing a microcomputer, to inject fuel compressed and transferred from a fuel pump (not shown in the figure) and then controlled to a predetermined pressure by a pressure regulator. Further, a water temperature sensor 17 is equipped for detecting a cooling water temperature Tw inside a cooling jacket of the engine 11, and a wide-range air-fuel ratio sensor 19 is equipped for linearly detecting an air-fuel ratio of the intake air-fuel mixture corresponding to the oxygen concentration in the exhaust in an exhaust passage 18. Further, a three-way catalyst 20 is equipped for purifying the exhaust by oxidizing the CO and HC and deoxidizing the NO$_x$ in the exhaust on the downstream side of the exhaust passage 18.

Figure 2:
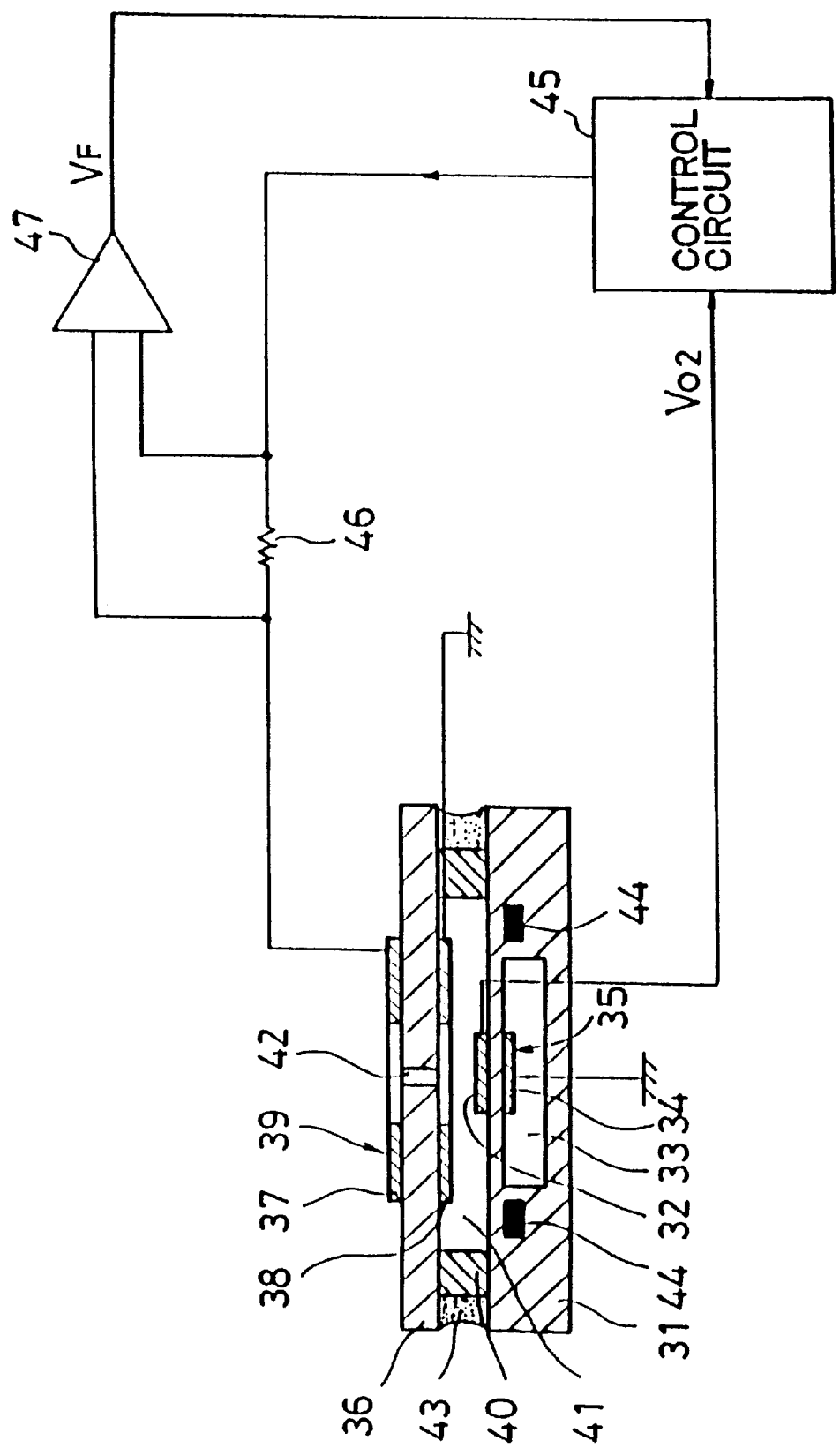
FIG. 2 shows the air-fuel ratio sensor and its peripheral circuit according to the embodiment of FIG. 1.

The structure of the wide-range air-fuel ratio sensor 19 will now be explained with reference to FIG. 2.

On top of a substrate 31 formed of a solid electrolyte material such as zirconia (ZrO$_2$) and the like is mounted a plus electrode 32 for measuring the oxygen concentration. Further, an air inlet hole 33 for introducing atmospheric air is formed to the substrate 31. A minus electrode 34 is mounted to the air inlet hole 33 so as to be opposite to the plus electrode 32.

In this way, the substrate 31, the plus electrode 32 and the minus electrode 34 constitute an oxygen concentration detecting unit 35.

Further, on both sides of a solid electrolyte member 36 made of zirconia and the like are mounted a pair of platinum pump electrodes 37 and 38, which constitute an oxygen pump unit 39.

The oxygen pump unit 39 is stacked to the upper area of the oxygen concentration detecting unit 35 through a rim-shaped spacer 40 formed of alumina and the like. Thereby, a sealed hollow chamber 41 is formed between the oxygen concentration detecting unit 35 and the oxygen pump unit 39. Moreover, an inlet hole 42 for introducing the exhaust of the engine to the hollow chamber 41 is formed to the solid electrolyte member 36 of the oxygen pump unit 39. Moreover, the outer peripheral area of the spacer 40 is filled with an adhesive 43 made of glass, thereby securing the sealing performance of the hollow chamber 41, and at the same time, fixing the substrate 31, the spacer 40 and the solid electrolyte 36 together. Here, the spacer 40 and the substrate 31 are simultaneously burned and bonded together, so the sealing performance of the hollow chamber 41 may be secured by adhering the spacer 40 and the solid electrolyte member 36. Further, the oxygen concentration detecting unit 39 is equipped with a warm-up heater 44 installed thereto.

The oxygen concentration of the exhaust introduced through the inlet hole 42 to the hollow chamber 41 is detected from a voltage of the plus electrode 32.

Actually, according to a difference in concentration of the oxygen in the atmosphere inside the air inlet hole 33 and the oxygen in the exhaust inside the hollow chamber 41, an oxygen ion current flows inside the substrate 31. Accompanying the current flow, the plus electrode 32 generates a voltage corresponding to the oxygen concentration in the exhaust.

According to the detected result, the current value flowing to the oxygen pump unit 39 is variably controlled so as to maintain the atmosphere inside the hollow chamber 41 to a constant value (for example, the theoretical air-fuel ratio). Based on the current value at that time, the oxygen concentration in the exhaust may be detected.

Actually, in order to maintain the oxygen concentration in the hollow chamber 41 to a constant value, the voltage of the plus electrode 32 is amplified by a control circuit 45, and then applied between the electrodes 37 and 38 through a voltage detection resistor 46.

For example, when detecting an air-fuel ratio in a lean region where the oxygen concentration in the exhaust is high, the pump electrode 37 mounted on the outer side is set as positive electrode and the pump electrode 38 on the chamber side is set as negative electrode, thereby applying a voltage. Then, the oxygen (oxygen ion O$^{2-}$) in proportion to the current is pumped out from the hollow chamber 41 to the exterior. When the applied voltage reaches a predetermined value or more, the flowing current reaches a limited value. By measuring the limited current value by the control circuit 45, the oxygen concentration in the exhaust, in other words, the air-fuel ratio, may be detected.

In contrast, when the pump electrode 37 is set as negative electrode and the pump electrode 38 as positive electrode to pump oxygen into the chamber 41, detection may be carried out in the rich air-fuel ratio region where the oxygen concentration in the exhaust is low.

Such limit current is detected by an output voltage $V_F$ of a differential amplifier 47 for detecting a voltage between terminals of the voltage detecting resistor 46.

Returning to FIG. 1, a crank angle sensor 21 is installed to a distributor (not shown in the figure). A crank unit angle signal output from the crank angle sensor 21 in synchronism with the engine rotation is counted for a given period of time or the cycle of a reference crank angle signal is measured, so as to detect an engine rotation speed Ne. Further, there is provided an outside air temperature sensor 22 for detecting the outside air temperature.

The control unit 16 computes and controls a fuel injection quantity of the fuel injection valve 15 and an ignition timing, and carries out the activation diagnosis on the air-fuel ratio sensor according to the present invention.

The activation diagnosis routine on the air-fuel ratio sensor according to a first embodiment of the present invention is explained below with reference to the flowcharts of FIGS. 3 and 4.

Figure 3:
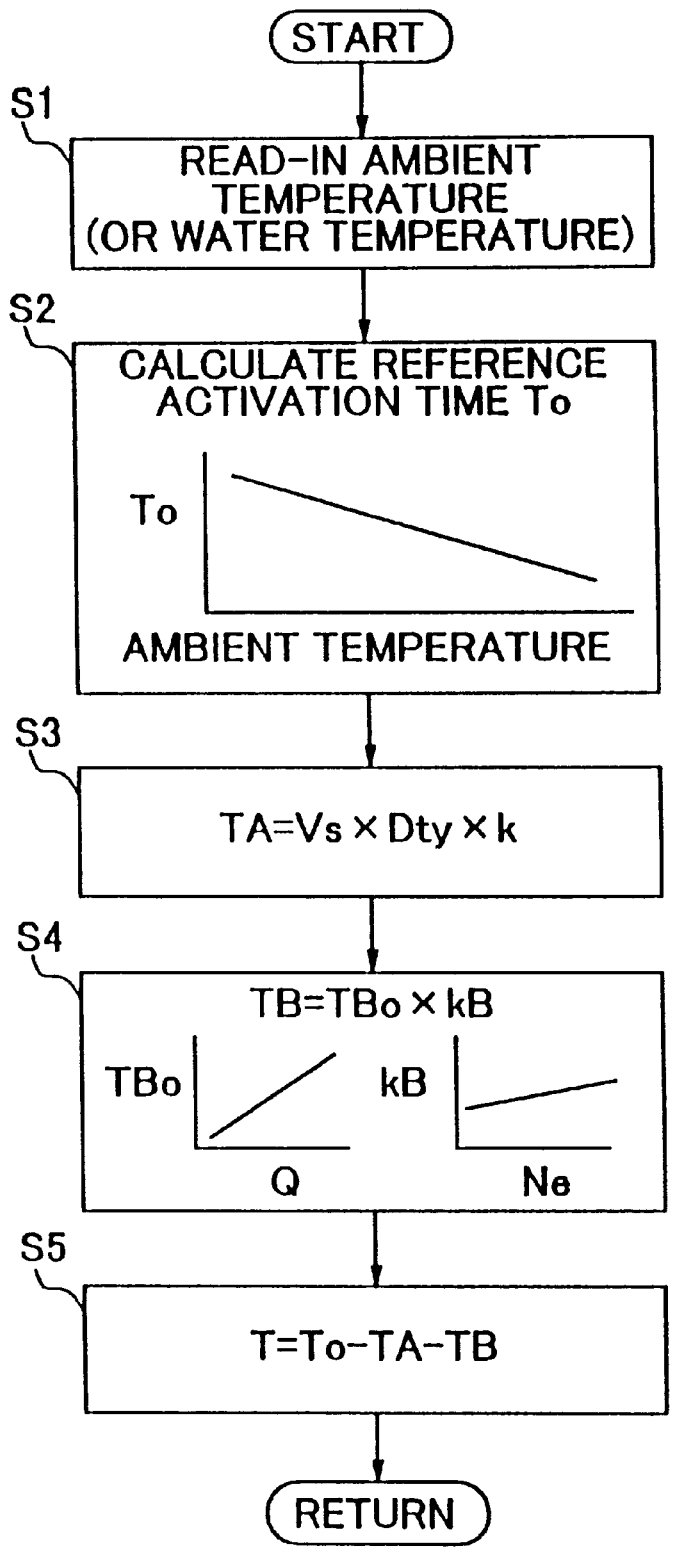
FIG. 3 is a flowchart showing the routine for calculating the activation time of the air-fuel ratio sensor according to a first embodiment.

FIG. 3 shows a routine for calculating a time T needed for the air-fuel ratio sensor to be activated after starting the engine operation.

In step (denoted as S in the drawings) 1, the outside air temperature detected by the outside air temperature sensor 22 (or the cooling water temperature detected by the water temperature sensor 17) is read in as an environmental temperature when starting the engine.

In step 2, a reference activation time To determined by the heat capacity of the air-fuel ratio sensor 19 is calculated by searching a map and the like based on the outside air temperature (or the water temperature). Actually, the lower the outside air temperature (or water temperature) is, the larger the heat radiation quantity from the air-fuel ratio sensor 19 is, so the reference activation time To needed for the activation is set to a larger value.

In step 3, an activation shortening time TA according to a heat generation quantity per unit time from a heater 44 installed to the air-fuel ratio sensor 19 is calculated by the following expression.

$$TA=Vs \text{ (battery voltage)} \times Dty \text{ (power supply duty to heater 44)} \times k \text{ (constant)}$$

In step 4, an activation shortening time TB corresponding to a heat quantity of the exhaust supplied to the air-fuel ratio sensor 19 is set by the following expression as a value calculated by multiplying a basic value TBo set in proportion to the intake air quantity Q as shown in the figure by a correction coefficient kB corresponding to the exhaust flow speed by the engine, rotation speed Ne.

$$TB=TBo \times kB$$

In step 5, the activation time T is calculated by the following expression.

$$T=To-TA-TB$$

Figure 4:
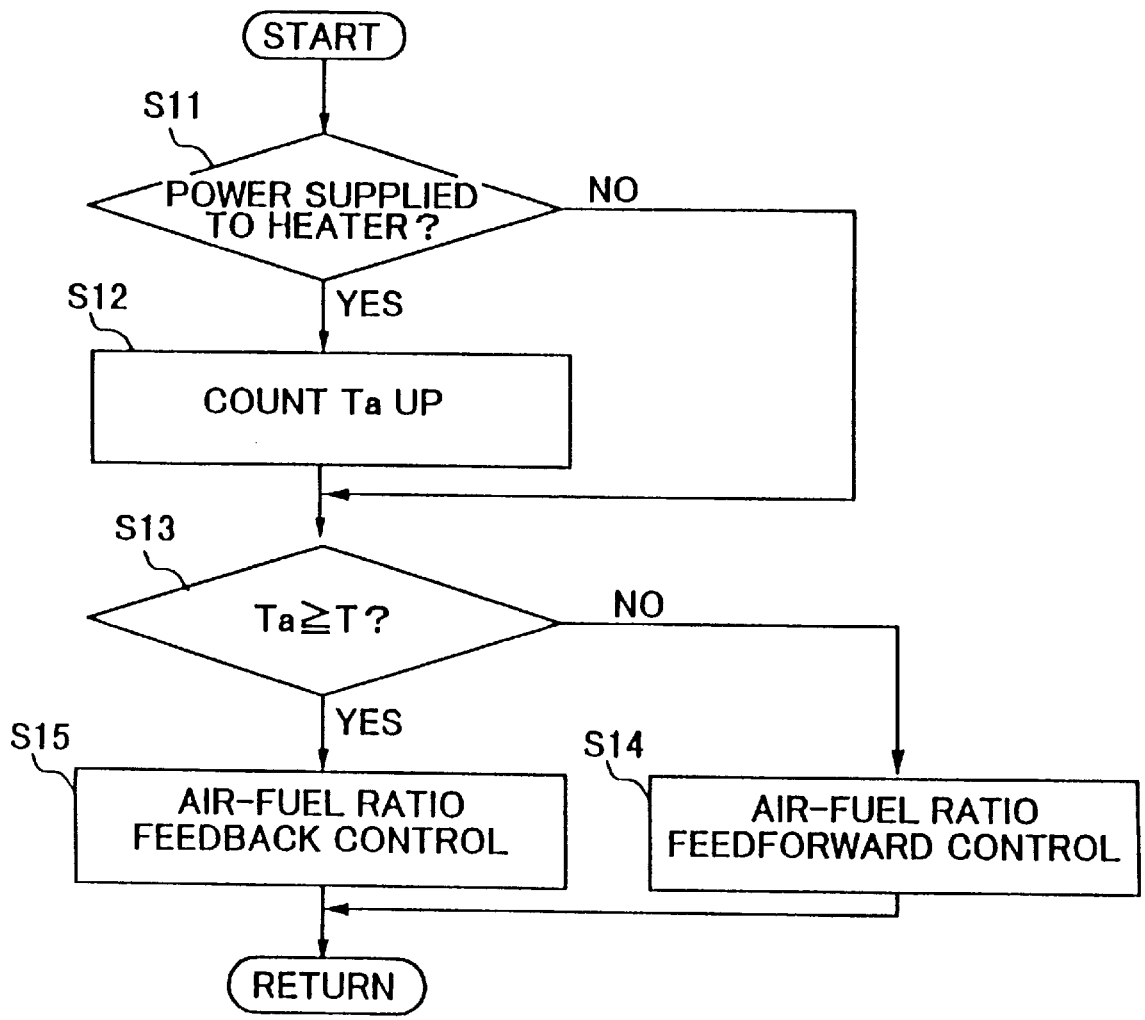
FIG. 4 is a flowchart showing the routine for starting the air-fuel ratio feedback control according to the first embodiment.

FIG. 4 shows a routine for starting the air-fuel ratio feedback control, based on the activation time T calculated as above.

In step 11, judgement is made on whether the power supply to the heater 44 installed to the air-fuel ratio sensor 19 is started or not (whether the operation of the engine is started or not).

When the judgement in step 11 is YES, then the procedure is advanced to step 12, where a timer Ta for measuring the time after starting the power supply is counted up.

In step 13, it is judged whether a value of the timer Ta has reached the activation time T or not.

When the value has not yet reached the activation time T, the procedure is advanced to step 14, where the air-fuel ratio is feedforward-controlled without using the value detected by the air-fuel ratio sensor 19. When the value has reached the activation time T, the procedure is advanced to step 15, where the air-fuel ratio feedback control utilizing the value detected by the air-fuel ratio sensor 19 is started.

In this way, the activation status of the wide-range type air-fuel ratio sensor 19 may be judged with high accuracy, and the air-fuel ratio feedback control may be started at the earliest time possible. Thereby, the exhaust emission performance may be improved greatly.

FIG. 5 shows an activation diagnosis routine of the air-fuel ratio sensor according to a second embodiment of the present invention. The hardware structure is similar to that of the first embodiment. The present routine starts simultaneously when power supply to the heater 44 is started, in other words, when engine operation is started.

In step 21, an output voltage $Vo_2$ of the oxygen concentration detecting unit 35 in the air-fuel ratio sensor 19 is read in.

In step 22, judgement is made on whether the output voltage $Vo_2$ is equal to or above a rich-side set voltage VRICH, and when it is determined that the voltage is below VRICH, the procedure is advanced to step 23, where judgement is made on whether the output voltage $Vo_2$ is equal to or below a lean-side set voltage VLEAN.

When it is judged that the output voltage $Vo_2$ exceeds the lean-side set voltage VLEAN, it is judged that the air-fuel ratio sensor 19 has not yet been activated, and the procedure is advanced to step 24 where the air-fuel ratio is feedforward-controlled.

Further, when it is judged in step 22 that the output voltage $Vo_2$ of the oxygen concentration detecting unit 35 is equal to or above the rich-side set voltage VRICH, or when it is judged in step 23 that the output voltage $Vo_2$ of the oxygen concentration detecting unit 35 is equal to or below the lean-side set voltage VLEAN, it is judged that the air-fuel ratio sensor is almost activated.

Next, in step 25, a timer TM for measuring elapsed time after the above-mentioned judgement is counted up. Then, the procedure is advanced to step 26, where judgement is made on whether the value of the timer TM has reached a predetermined value or not, in other words, whether a predetermined time TAF has passed.

Before the passing of the predetermined time TAF, the procedure is advanced to step 24 where the feedforward control of the air-fuel ratio is continued. However, when the predetermined time TAF has passed, it is diagnosed that the air-fuel ratio sensor 19 has been activated completely, and the procedure is advanced to step 27, where the air-fuel ratio feedback control is started based on a detected value $V_F$ of the air-fuel ratio sensor 19.

A change in the output voltage $Vo_2$ of the oxygen concentration detecting unit 35 and the output voltage $V_F$ of the air-fuel ratio sensor 19 while performing the air-fuel ratio feedback control mentioned above is shown in FIG. 6.

The predetermined time TAF may also be set based on the heat transferred to and from the air-fuel ratio sensor 19, or the time for complete activation may be set through highly accurate estimation performed based on at least one of the following parameters; the heat radiation quantity from the air-fuel ratio sensor due to the engine temperature, or the heat quantity supplied to the air-fuel ratio sensor due to the heat generation quantity of the heater or the heat quantity of the exhaust.

In a simplified example, the construction may be such that when it is judged that the output voltage $Vo_2$ of the oxygen concentration detecting unit 35 is equal to or above the rich-side set voltage VRICH or equal to or below the lean-side set voltage VLEAN, in other words, when it is judged that the air-fuel ratio sensor is almost activated, the air-fuel ratio feedback control is started immediately.

Further, when monitoring the output voltage $Vo_2$ of the oxygen concentration detecting unit 35 functioning as the oxygen sensor, the oxygen pump unit 39 should preferably not be activated, so that the output voltage $Vo_2$ of the oxygen concentration detecting unit 35 is fixed without fail to either a value equal to or above the rich-side set voltage VRICH or a value equal to or under the lean-side set voltage VLEAN.

What we claimed are:

1. An activation diagnosis method for a wide-range type air-fuel ratio sensor, said air-fuel ratio sensor being equipped with an oxygen concentration detecting unit formed of a solid electrolyte and outputting detection signals corresponding to oxygen concentration inside a hollow chamber to which exhaust of an internal combustion engine is introduced, and an oxygen pump unit for pumping oxygen into or out of said hollow chamber by controlling a current being applied to a solid electrolyte wall separating said hollow chamber and the exhaust side of said engine so as to control the oxygen concentration inside said hollow chamber to predetermined oxygen concentration, said air-fuel ratio sensor detecting the current being applied to said solid electrolyte wall to output an air-fuel ratio signal corresponding to the oxygen concentration in the exhaust; said activation diagnosis method comprising the steps of:

monitoring an output voltage of said oxygen concentration detecting unit after the starting of operation of said engine;

judging whether or not said output voltage of said oxygen concentration detecting unit is fixed to either a value equal to or above a rich-side set voltage or a value equal to or below a lean-side set voltage; and diagnosing that said air-fuel ratio sensor is activated under the condition that a status is detected where the output voltage of said oxygen concentration detecting unit is fixed to either a value equal to or above a rich-side set voltage or a value equal to or below a lean-side set voltage.

2. An activation diagnosis method for an air-fuel ratio sensor according to claim 1, wherein the activation of said air-fuel ratio sensor is diagnosed when a predetermined time has passed after detecting said status where the output voltage of said oxygen concentration detecting unit fixed to either a value equal to or above a rich-side set voltage or a value equal to or below a lean-side set voltage.

3. An activation diagnosis method for an air-fuel ratio sensor according to claim 2, wherein said predetermined time is set based on the heat transferred to and from the air-fuel ratio sensor.

4. An activation diagnosis apparatus for a wide-range type air-fuel ratio sensor, said air-fuel ratio sensor being equipped with an oxygen concentration detecting unit formed of a solid electrolyte and outputting detection signals corresponding to oxygen concentration inside a hollow chamber to which exhaust of said internal combustion engine is introduced, and an oxygen pump unit for pumping oxygen into or out of said hollow chamber by controlling a current being applied to a solid electrolyte wall separating said hollow chamber and the exhaust side of said engine so as to control the oxygen concentration inside said hollow chamber to predetermined oxygen concentration, said air-fuel ratio sensor detecting the current being applied to said solid electrolyte wall to output an air-fuel ratio signal corresponding to the oxygen concentration in the exhaust; said diagnosis apparatus comprising:

an output voltage monitoring device which monitors an output voltage of said oxygen concentration detecting unit after the starting of operation of said engine;

a judging device which judges whether or not said output voltage of said oxygen concentration detecting unit being monitored by said output voltage monitoring device is fixed to either a value equal to or above a rich-side set voltage or a value equal to or below a lean-side set voltage; and a diagnosis device which diagnoses that said air-fuel ratio sensor is activated under the condition that said judging device detects a status where the output voltage of said oxygen concentration detecting unit is fixed to either a value equal to or above a rich-side set voltage or a value equal to or below a lean-side set voltage.

5. An activation diagnosis apparatus for an air-fuel ratio sensor according to claim 4, wherein the activation of said air-fuel ratio sensor is diagnosed when a predetermined time has passed after detecting said status where the output voltage of said oxygen concentration detecting unit is fixed to either a value equal to or above a rich-side set voltage or a value equal to or below a lean-side set voltage.

6. An activation diagnosis apparatus for an air-fuel ratio sensor according to claim 5, wherein said predetermined time is set based on the heat transferred to and from said air-fuel ratio sensor.

7. An activation diagnosis apparatus for a wide-range type air-fuel ratio sensor, said air-fuel ratio sensor being equipped with an oxygen concentration detecting unit formed of a solid electrolyte and outputting detection signals corresponding to oxygen concentration inside a hollow chamber to which exhaust of said internal combustion engine is introduced, and an oxygen pump unit for pumping oxygen into or out of said hollow chamber by controlling a current being applied to a solid electrolyte wall separating said hollow chamber and the exhaust side of said engine so as to control the oxygen concentration inside said hollow chamber to predetermined oxygen concentration, said air-fuel ratio sensor detecting the current being applied to said solid electrolyte wall to output an air-fuel ratio signal corresponding to the oxygen concentration in the exhaust; said diagnosis apparatus comprising:

an output voltage monitoring means for monitoring an output voltage of said oxygen concentration detecting unit after the starting of operation of said engine;

a judging means for judging whether or not said output voltage of said oxygen concentration detecting unit being monitored by said output voltage monitoring means is fixed to either a value equal to or above a rich-side set voltage or a value equal to or below a lean-side set voltage; and a diagnosis means for diagnosing that said air-fuel ratio sensor is activated under the condition that said judging means detects a status where the output voltage of said oxygen concentration detecting unit is fixed to either a value equal to or above a rich-side set voltage or a value equal to or below a lean-side set voltage.

8. An activation diagnosis apparatus for an air-fuel ratio sensor according to claim 7, wherein the activation of said air-fuel ratio sensor is diagnosed when a predetermined time has passed after detecting said status where the output voltage of said oxygen concentration detecting unit is fixed to either a value equal to or above a rich-side set voltage or a value equal to or below a lean-side set voltage.

9. An activation diagnosis apparatus for an air-fuel ratio sensor according to claim 8, wherein said predetermined time is set based on the heat transferred to and from said air-fuel ratio sensor.

* * * * *